United States Patent [19]

Fox

[11] Patent Number: 4,751,292

[45] Date of Patent: Jun. 14, 1988

[54] ADAMANTYL PURINES

[75] Inventor: Juan E. Fox, Danville, Calif.

[73] Assignee: The Plant Cell Research Institute, Inc.

[21] Appl. No.: 751,619

[22] Filed: Jul. 2, 1985

[51] Int. Cl.$^4$ .................. C07D 473/34; A61K 31/70; A61K 31/52

[52] U.S. Cl. ...................................... 536/24; 544/277; 544/265; 536/25; 71/92

[58] Field of Search ............... 544/267, 277, 265, 276; 514/263; 536/24, 25; 71/92

[56] References Cited

U.S. PATENT DOCUMENTS

| | | | |
|---|---|---|---|
| 3,150,124 | 9/1964 | Svarnas | 260/211.5 |
| 3,257,456 | 6/1966 | Smith | 260/586 |
| 3,532,748 | 10/1970 | Smith | 260/563 |
| 3,890,299 | 6/1975 | Fox | 260/211.5 R |
| 3,926,949 | 12/1975 | Fox | 260/211.5 R |
| 4,714,697 | 12/1987 | Trivedi et al. | 536/24 |

OTHER PUBLICATIONS

Letham, Cytokinins in Phytohormones and Related Compounds-A Comprehensive Treatise, vol. I, The Biochemistry of Phytohormones, and Related Compounds, Elsevier/North Holland Medical Press, 1978, Amsterdam.

*Primary Examiner*—Nicholas S. Rizzo
*Attorney, Agent, or Firm*—Ciotti & Murashige, Irell & Manella

[57] ABSTRACT

The present invention comprises novel adamantyl purine derivatives, in which the purine ring is substituted at the 6-position with a moiety incorporating an adamantane ring system. The purine may also be substituted at the 9-position with a carbohydrate, to give a nucleoside analog, or may be unsubstituted at that position.

The substituent at the 6-position contains an adamantane ring system, either substituted or unsubstituted, in which a linker connects a carbon atom in the adamantane ring system with the 6-carbon of the purine ring. This linker consists of a combination of a heteroatom such as N, O or S, which is directly connected to the purine, and a short (five or less) atom chain, consisting either of carbon or other atoms such as N, O or S, with or without additional pendant moieties, which is connected either to the secondary or tertiary carbon of the adamantane ring system. The adamantane ring system itself may be unsubstituted, or substituted with a wide variety of non-ionic groups.

11 Claims, No Drawings

ADAMANTYL PURINES

FIELD OF THE INVENTION

The present invention relates generally to novel purine derivative chemical compounds that are useful in stimulating growth and cell division in plants. More specifically, the present invention relates to novel adenine-type purine derivatives that are substituted at the 6-position with moieties containing an adamantyl ring system.

BACKGROUND OF THE INVENTION

As is well known, cytokinins are plant hormones that act in concert with other plant hormones, such as auxins, in regulating many aspects of plant growth and development. Operationally, naturally occurring and synthetic compounds are defined as cytokinins if they promote growth and cell division (hence the name cytokinin, from cytokinesis) of cultured excised plant tissues when such compounds are added to a nutrient medium (containing auxin, vitamins, mineral salts, and sucrose, etc.) upon which the excised tissues are being grown.

Structurally, most cytokinins are derivatives of an adenine-type purine molecule in which the nitrogen at the sixth position is substituted with certain well defined side chain substituents such that the resulting molecules have biological activity similar to that exhibited by the first discovered substance in this series, kinetin. Since the initial discovery of kinetin, a wide variety of cytokinins have been synthesized and studied. As a result of these studies it is now generally known that the type of side chain constituents at $N_6$ which confer cytokinin activity to adenine are non-polar branched or straight chain aliphatic or aromatic moieties. For example, see Letham, D. S. "Cytokinins" in *Phytohormones and Related Compounds - A Comprehensive Treaties*, Vol. 1, "The Biochemistry of Phytohormones and Related Compounds", (edited by D. J. Letham, P. B. Goodwin and T. J. V. Higgins), Elsevier/North Holland Medical Press, 1978, Amsterdam.

One of the most important properties of the cytokinins is their ability to regulate development and organ formation in tissue cultures. Practically speaking, this cytokinin effect enables agriculturalists to use these compounds to produce large numbers of genetically engineered plants.

It is known that some ring substituents confer cytokinin activity on adenine if these substituents are linked at the $N_6$ position on the adenine moiety. However, until the present invention it was not known that adamantane and its derivatives, when linked to adenine at the $N_6$ position, would also confer cytokinin activity to the adenine molecule.

It is an object of the present invention to provide novel adamantyl purine compounds in which the purine ring is substituted at the 6-position with a moiety incorporating an adamantane ring system.

It is a further object of the present invention to provide novel adamantyl purine compounds in which the 6-position of the purine ring is substituted with a moiety incorporating an adamantane ring system, and the 9-position of the purine ring is substituted with a carbohydrate.

It is a further object of the present invention to provide novel adamantyl purine compounds in which the purine is substituted at the 6-position with an adamantane ring system, either substituted or unsubstituted, and a linker connects the carbon atom in the adamantane ring system with the 6-carbon of the purine ring.

It is a further object of the present invention to provide novel adamantyl purine compounds in which the 6-position of the purine is substituted with an adamantane ring system, either substituted or unsubstituted; the 9-position of the purine is substituted with a carbohydrate; and a linker connects the carbon atom in the adamantane ring system with the 6-carbon of the purine ring.

It is an object of the present invention to provide novel adamantyl adenine compounds in which the adenine ring is substituted at the 6-position with a moiety incorporating an adamantane ring system.

It is a further object of the present invention to provide novel adamantyl adenine compounds in which the 6-position of the adenine ring is substituted with a moiety incorporating an adamantane ring system, and the 9-position of the adenine ring is substituted with a carbohydrate.

It is a further object of the present invention to provide novel adamantyl adenine compounds in which the adenine is substituted at the 6-position with an adamantane ring system, either substituted or unsubstituted, and a linker connects the carbon atom in the adamantane ring system with the 6-carbon of the adenine ring.

It is a further object of the present invention to provide novel adamantyl adenine compounds in which the 6-position of the adenine is substituted with an adamantane ring system, either substituted or unsubstituted; the 9-position of the adenine is substituted with a carbohydrate; and a linker connects the carbon atom in the adamantane ring system with the 6-carbon of the adenine ring.

It is an object of the present invention to provide novel adamantyl purine compounds which exhibit growth regulatory activity in plants.

It is still another object of the present invention to provide novel adamantyl adenine compounds which exhibit enhanced promotion of growth in plant cells.

BRIEF DESCRIPTION OF THE INVENTION

The present invention comprises novel adamantyl purine derivatives, in which the purine ring is substituted at the 6-position with a moiety incorporating an adamantane ring system. The purine ring may also be substituted at the 9-position with a carbohydrate, to give a nucleoside analog, or may be unsubstituted at that position.

The substituent at the 6-position contains an adamantane ring system, either substituted or unsubstituted, in which a linker connects a carbon atom in the adamantane ring system with the 6-carbon of the purine ring. This linker consists of a combination of a heteroatom such as N, O or S, which is directly connected to the purine, and a short (four or less) atom chain, consisting either of carbon or other atoms such as N, O or S, with or without additional pendant moieties, which is connected either to the secondary or tertiary carbon of the adamantane ring system. The adamantane ring system itself may be unsubstituted, or substituted with a wide variety of non-ionic groups.

The present invention includes compounds having the general formulas as shown in Structures I and II:

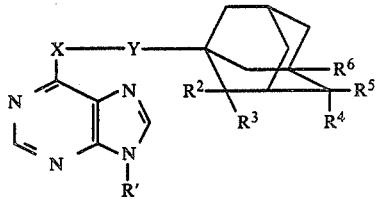

Structure I

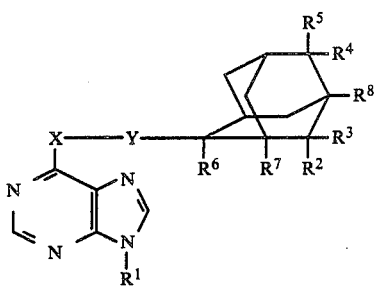

Structure II wherein
- $R^1$ is H or a monosaccharide selected from the group comprised of glucose, fructose, ribose, 2-deoxyribose, mannose, galactose, xylose, and arabinose;
- X is a heteroatom selected from the group comprised of N, O and S;
- Y is a linker group consisting of a linear arrangement of from one to five atoms, with or without additional pendant substituents, wherein said linker group is selected from the group comprised of: alkyl carbon; substituted alkyl carbon, with substituents selected from the group comprised of alkyl, aryl, hydroxyl, alkoxy, aryloxy, halogen, nitro, amino, cyano, carboxyalkyl, carboxamido, thio, alkylthio, and arylthio; carbonyl; carboxyalkyl; carboxamido; oxygen (as an ether); amino; thio; vinyl; and acetylenyl groups;
- $R^2$, $R^3$, $R^4$, $R^5$ are independently H; or monovalent radicals selected from the group comprised of alkyl, substituted alkyl, aryl, hydroxyl, alkoxy, aryloxy, alkylidene, vinyl, acetylenyl, amino, nitro, cyano, carboxyalkyl, carboxamido, halo, thiol and thioether; or divalent radicals selected from the group comprised of oxo, alkylidene and imino; and
- $R^6$, $R^7$ and $R^8$ are independently H; or monovalent radicals selected from the group comprised of alkyl, substituted alkyl, aryl, halo, hydroxyl, alkoxy or aryloxy, vinyl, acetylenyl, amino, cyano, nitro, carboxyalkyl, carboxamido, thio and alkylthio.

In a preferred form, the present invention comprises novel adamantyl adenine compounds of the formula:

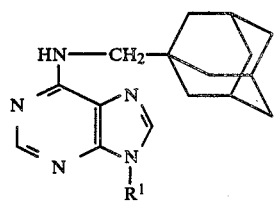

wherein $R^1$ is H or a monosaccharide selected from the group consisting of glucose, arabinose, galactose, ribose, 2-deoxyribose, mannose, fructose and xylose.

DETAILED DESCRIPTION OF THE INVENTION

With the foregoing in mind, the following discussion will serve to set forth detailed embodiments of the present invention in light of the above generic disclosure.

The novel cytokinins of the present invention are comprised of adamantane, or an adamantane derivative, linked to a purine molecule at the 6 position via a linker group. The adamantane moiety can be linked to the 6 position on the purine moiety by any suitable covalent linkage group attached via a heteroatom (such as N, O, or S) on the purine ring. For use in the present invention suitable linkage groups include methylene, ethylene, propylene or other alkyl, carbonyl, carboxamido, carboxyalkyl, ether, sulfonamido, arylthio, amino, vinyl, alkenyl, alkynyl, thio ethers, plus alkyl linkages which are substituted with alkyl, aryl, hydroxyl, alkoxy, aryloxy, halogen, nitro, amino, cyano, carboxyalkyl, carboxamido, thio, alkylthio and arylthio functionalities, and other groups known to those skilled in the art. Ethylene or methylene linkage groups are especially preferred in constructing the novel cytokinins of the present invention. Also preferred is the 6-amino purine (adenine) moiety. Other purines, such as hypoxanthine and thiohypo-xanthine can also be coupled to adamantane derivatives to prepare effective compounds that are within the scope of the invention.

A wide number of substituents at the 6 position will confer plant-growth promoting properties on purines. Given the general rule that the most effective cytokinins have non-polar 6 substituents, those skilled in the art can readily prepare a large number of useful compounds. Although adenine-cytokinins are well known in the art and adamantane derivatives are also well known, prior to the present invention it was not known that these groups could combine to create new, growth-enhancing compounds. By way of example, we have prepared 6-(1-adamantylmethylamino)purine (MAAP) and demonstrated its effectiveness in promoting plant growth, even at low concentrations.

It is known that the substituent at $N_9$ of the purine moiety can affect cytokinin potency. It is also known that the presence of a polar group, such as a monosaccharide, attached to the purine tends to improve the plant cell uptake of cytokinin and therefore leads to increased efficacy of the resultant compounds. For example, U.S. Pat. No. 3,890,299. In preferred forms of the the present invention, the $N_9$ substituent of purine will either be hydrogen, or a monosaccharide such as ribose, glucofuranose, glucopyranose, galactose, fructose, mannose, or xylose. Although the precise mode of action of the $N_9$-type monosaccharide containing cytokinins is unknown, it is believed that the the presence of the monosaccharide improves the water solubility of the cytokinin, thus permitting an overall superior biological effect (plant growth regulatory activity) to be achieved. Again, by way of example, we have prepared MAAP-ribose, a 9-ribose derivative of MAAP, and shown it to be effective in promoting plant growth.

The novel adamantyl purine compounds of the present invention can be synthesized from readily available or readily synthesized starting materials, using standard chemical methods of synthesis. For example, the compounds of the present invention can be synthesized from 6-chloropurine or from a suitable derivative of 6-chloropurine which already contains a desired $N_9$ substituent. One such suitable derivative of 6-chloropurine is 6-chloropurine-9-riboside. The chloropurine, or the chloropurine derivative, can then be condensed with a suitable adamantane moiety, containing a suitable linkage group, in an aqueous phosphate solution or other suitable solvent such as ethylene dichloride or dimethylamine. 1-adamantylmethylamine is an especially preferred adamantane moiety for use in such a condensation reaction. The condensation reaction is allowed to proceed until condensation between the reactants has occurred (usually 1-3 hours), after which the product usually precipitates. At that time the product can be filtered off and recrystallized. For purposes of illustration, the syntheses of representative compounds 6-(1-adamantylmethylamino)purine and its 9-beta-ribofuranoside are shown infra in Examples I and II.

When used as cytokinins, the compounds of the present invention are suitably administered by dissolving them in water and administering the aqueous adamantyl adenine solution to plants, in an effective therapeutic amount, by any conventional, acceptable, horticultural means. For example, an aqueous solution of the compound can be directly administered to a plant by spraying onto the leaves together with a suitable wetting agent such as polyoxyethylene sorbitan monolaurate. (Polyoxyethylene sorbitan monolaurate is available from Bio-Rad Laboratories, Richmond, Calif. 94804 under the trade name "Tween-20".)

Normally, while the dosage range for the adamantyl adenine compounds of this invention will vary, depending upon the plant employed and the physiological requirements of the plant, as a basic guideline, an amount of about from 0.1 micrograms/gram of plant weight to 0.1 milligram/gram of plant weight will suffice.

The cytokinin activity of the novel compounds of the present invention can be tested by any of a number of standard assays. Two such well known and widely used assays are the tobacco pith tissue assay as described by Murashige and Skoog (1962) *Physiol, Plant,* 15:473-497, and the soybean callus tissue assay, described by Miller (1963) *Modern Methods of Plant Analysts,* 6:194-202. In these assays the tissues are normally grown for a period of two to four weeks on media in which the test substance has been incorporated, after which fresh and dry weights are compared with suitable controls.

By way of example, the effect of a representative adamantyl-purine-nucleoside compound of the present invention (e.g. 6-(1-adamantylmethylamino)purine, referred to herein as Compound 1) on the growth of both tobacco and soybean tissue is shown infra in Example IV. As the results disclosed therein indicate, when assayed with tobacco callus tissue, Compound 1 was about twice as effective as a prior art cytokinin control compound (6-benzylaminopurine) in promoting plant growth. In a parallel experiment using soybean callus, when compared with a cytokinin control, Compound 1 was shown to be about 80% as effective.

Another frequently performed assay to test cytokinin activity is based on the observation by Richmond and Lang that cytokinins will delay the onset of senescence in many types of leaves. See, for example, Osborne and McCalla (1961) *Plant Physiol,* 36:219-221. To illustrate the effect of a representative adamantyl adenine compound of the present invention in this regard, the effect of 6-(1-adamantylmethylamino)purine, (referred to herein as Compound 2) on chlorophyll retention in senescing wheat leaves is described in Example III, infra. As the results disclosed therein indicate, at a concentration of $1.1 \times 10^{-5}$ M, Compound 2 caused approximately the same chlorophyll retention as the prior art compound (6-benzylaminopurine) did at a concentration of $1.9 \times 10^{-5}$ M.

Without further elaboration, it is believed that one of ordinary skill in the art can, using the preceding description, utilize the present invention to its fullest extent. The following examples are included for illustrative purposes only and therefore are not to be construed as being limitative in any way of the remainder of the specification and claims.

EXPERIMENTAL METHODS

Examples I and II illustrate synthesis of representative adamantyl-purine-nucleoside compounds of the present invention. In these examples synthetic products were purified and analyzed by high performance liquid chromotography (HPLC) on a $C_{18}$ reversed phase column, Beckman Ultrasphere ODS. Ultraviolet spectra were taken on a Cary 219. Mass spectra when obtained on a VG 7070E using electron impact ionization. Unless otherwise indicated, all reference to temperatures denote Centigrade.

Examples III and IV illustrate the biological activity of representative cytokinins of the present invention using standard tissue culture assays for growth enhancement in tobacco tissue, growth enhancement in soybean tissue, and chlorophyll retention in senescing wheat leaves.

EXAMPLE 1

Preparation of 6-(1-Adamantylmethylamino)Purine (MAAP) (Compound 1)

The method of synthesizing Compound 1 is based on a previously reported (Fox, J. E. (1966) *Plant Physiol.* 41:75) modification of the Daly and Christensen synthesis of 6-substituted amino purines (Daly, J. and Christensen B. (1956) *J. Org. Chem.* 21:177).

To a solution of 773 mg (5 mmols) 6-chloropurine (Sigma, St. Louis, MO) in 50 ml aqueous 0.1 M $Na_2HPO_4$, there was added 400 microliters (2.67 mmols) 1-adamantyl-methylamine (Aldrich Chemical Co., Milwaukee, Wis.). This mixture was refluxed for three hours. The precipitate which formed during reflux was then filtered and washed with deionized water at 25° C. The product could be dissolved in warm ethanol and was recrystallized from 50 percent ethanol/water. Trace impurities were removed by purification on HPLC. M. P. 287° C. (cor). UV:Lambda max (extinction coefficient): MeOH-266.5 (17,000), 278 sh, 211.5; Water (pH 7.5) - 279 sh, 269, 210; pH 10.5 ($NH_4OH$) - 282 sh, 279, 274, 215; pH 5.5 - 269, 210; pH 1(HCl) - 279, 270, 205.5. Mass Spec (major peaks): 283 ($MI^+$, 35% of base), 267, 148, 135.

EXAMPLE II

Preparation of 6-(1-Adamantylmethylamino) Purine-9-Beta-Ribofuranoside (MAAP-Riboside)

Compound 2

MAAP-Riboside was prepared using a method analogous to that used for the syntheses of MAAP.

To a solution of 611 mg (2.13 micromol) of 6-chloropurine riboside (Sigma Chemical Co., St. Louis, Mo.) in 50 ml of aqueous 0.1 M $Na_2HPO_4$ there was added 750 microliters (5 mmols) of 1-adamantylmethylamine as above. The mixture was stirred for one hour at 85° C. After decanting the supernatant solution, the reaction precipitate was dissolved in methanol. The product was purified by preparative HPLC. Yield—93 percent. M. P. 266° (dec., cor.). UV: EtOH-279, 267-68, 213; Water (pH 7.0) - 279 sh, 268 (17,000), 212; 0.1M KOH-279 sh, 269; 0.1 M HlCl-266. Mass spectrum: 458 (MI+15% of base), 416, 12, 284, 135.

EXAMPLE III

THE EFFECT OF MAAP-RIBOSIDE ON CHLOROPHYLL RETENTION IN SENESCING WHEAT LEAVES

The biological activity of MAAP-Riboside (Compound 2) was determined using a standard chlorophyll retention assay to test chlorophyll retention in senescing wheat leaves. See Kende, H. (1961) "Preservation of Chlorophyll in Leaf Sections by Substances Obtained from Root Exudate", Science 145:1066-1067.

Senescing wheat leaves were treated with MAAP-Riboside, water, or a cytokinin control. After separation of chlorophyll from other plant material, the optical density of the extracts was measured at 661 nanometers, subtracting the value measured for leaves treated only with deionized water. Table 1 shows that MAAP-Riboside, at a concentration of $1.1 \times 10^{-5}$ M, caused approximately the same chlorophyll retention as that obtained when the leaves were treated with a prior art compound (6-benzylaminopurine) at a concentration of $1.9 \times 10^{-5}$ M.

TABLE 1

CHLOROPHYLL RETENTION IN SENESCING WHEAT LEAVES

| MAPP-Riboside[a] | OD661[b] |
|---|---|
| $1.1 \times 10^{-8}$ M | 10 |
| $1.1 \times 10^{-7}$ M | 110 |
| $1.1 \times 10^{-6}$ M | 350 |
| $1.1 \times 10^{-5}$ M | 640 |
| cytokinin control[c] | 630 |

[a] concentration of added MAAP-Riboside
[b] optical density at 661 mm minus water control
[c] 6-benzylamino adenine, $1.9 \times 10^{-5}$ M

EXAMPLE IV

BIOLOGICAL ACTIVITY OF MAAP SHOWING CYTOKININ ACTIVITY IN SOYBEAN AND TOBACCO TISSUE

The biological activity of MAAP (Compound 1) was determined by the standard soybean "callus" cytokinin assay disclosed by Miller, C.O., in "Modern Methods of Plant Analysis," (Linskens, H. F. and Tracy, M. D., Editors), Volume VI, pages 194-202, Springer, Berlin, 1963.

This standard soybean callus assay and the related tobacco callus assay consist of growing the soybean or tobacco callus in tissue culture on a basal medium to which an auxin and varying proportions of test cytokinin compounds have been added. After 30 days of growth, the fresh weight (per piece) of plant callus is determined, after which the sample is dried and again weighed. The results of both assays are summarized in Table II below.

The tobacco callus results indicate that when $1.5 \times 10^{-7}$ M MAAP was included in the growth medium, tobacco callus achieved a fresh tissue weight of 3,000 milligrams, and a dry tissue weight of 150 milligrams. In comparison, a basal control grown on medium which did not contain cytokinin achieved a fresh tissue weight of 100 milligrams and a dry tissue weight of 5 milligrams. The results from the cytokinin control indicate that addition of a prior art compound (6-benzylaminopurine) at about $2 \times 10^{-6}$ M gave a fresh tissue weight of 1300 milligrams and a dry tissue weight of 83 milligrams. Thus in the tobacco callus assay, the optimal concentration of MAAP was about two times more effective than the cytokinin control in promoting growth.

In a parallel soybean callus experiment, when $1.5 \times 10^{-7}$ M MAAP was included in the growth medium, soybean callus achieved a fresh tissue weight of 540 milligrams, and a dry tissue weight of 39 milligrams. In comparison, a basal control grown on medium which did not contain cytokinin achieved a fresh tissue weight of 10 milligrams and a dry tissue weight of 2.7 milligrams. In the cytokinin control, addition of a prior art compound (6-benzylaminopurine) at about $2 \times 10^{-6}$ M gave a fresh tissue weight of 740 milligrams and a dry tissue weight of 47.3 milligrams. Thus in the soybean callus assay, the optimal concentration of MAAP was 75 to 80 percent as effective as the cytokinin control in promoting growth.

TABLE 2

CYTOKININ ACTIVITY IN SOYBEAN AND TOBACCO TISSUE

| MAAP CONCENTRATION | TISSUE-WEIGHT (MG) | | | |
|---|---|---|---|---|
| | SOYBEAN | | TOBACCO | |
| | FRESH | DRY | FRESH | DRY |
| Basal Control | 10 | 2.7 | 100 | 5 |
| $1.5 \times 10^{-9}$ M | 330 | 27 | 100 | 10 |
| $3 \times 10^{-8}$ M | 340 | 26.7 | 250 | 17 |
| $1.5 \times 10^{-7}$ M | 540 | 39 | 3,000 | 150 |
| $3 \times 10^{-7}$ M | 360 | 26 | 2,900 | 150 |
| $1.5 \times 10^{-6}$ M | 80 | 5.3 | 1,600 | 96 |
| cytokinin control | 740 | 47.3 | 1,300 | 83 |

SUMMARY

From the foregoing description, one of ordinary skill in the art can easily ascertain that the essential characteristic of the instant invention is the disclosure of novel adamantyl purine compounds comprised of adamantane or its derivatives linked to an purine moiety at the 6 position via a heteroatom such as N, O or S. Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An adamantyl purine compound of the formula

Structure I

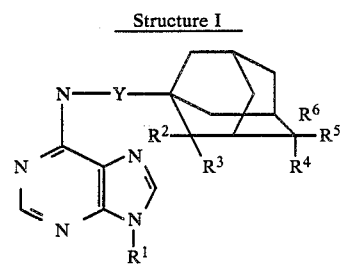

or

-continued
Structure II

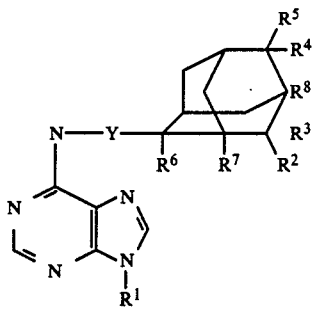

wherein
- $R_1$ is H or a monosaccharide selected from the group consisting of glucose, fructose, ribose, 2-deoxyribose, mannose, galactose, xylose and arabinose;
- Y is a linker which is a saturated alkylene (1-5C) which is unsubstituted or is substituted with substituents selected from the group consisting of alkyl, hydroxyl, alkoxy, halogen, nitro, amino, cyano, carboxyalkyl, carboxamido, thio, and alkylthio; or wherein Y is a linear arrangement of 1-5 atoms which includes moiety selected from the group consisting of carbonyl; carboxyalkyl; carboxamido, oxygen (as an ether); amino; thio; vinyl; and acetylenyl groups;
- $R^2$, $R^3$, $R^4$, $R^5$ are independently two H radicals, H and a monovalent radical selected from the group consisting of alkyl, alkyl, hydroxyl, alkoxy, vinyl, acetylenyl, amino, nitro, cyano, carboxyalkyl, carboxamido, halo, thiol and thioether; or a divalent radical selected from the group consisting of oxo, alkyldiene and imino; and
- $R^6$, $R^7$ and $R^8$ are independently H or monovalent radicals selected from the group consisting of alkyl, alkyl, halo, hydroxyl, alkoxy, vinyl, acetylenyl, amino, cyano, nitro, carboxyalkyl, carboxamido, thio and alkylthio.

2. A adamantyl adenine compound having the formula:

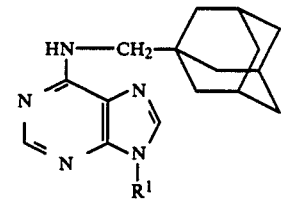

wherein $R^1$ is H or a monosaccharide selected from the group consisting of glucose, arabinose, galactose, ribose, 2-deoxyribose, mannose, fructose and xylose.

3. The compound 6-(1-adamantylmethylamino)purine.

4. The compound 6-(1-adamantylmethylamino)purine-9-beta-ribofuranoside.

5. The compound of claim 1 wherein $R^2$, $R^3$, $R^4$, $R^5$, $R^6$, $R^7$ and $R^8$ are H.

6. The compound of claim 1 wherein Y is an unsubstituted alkylene of 1-5C.

7. The compound of claim 5 wherein Y is an unsubstituted alkylene of 1-5C.

8. The compound of claim 1 wherein Y is a linear arrangement of 1-5 atoms which comprises a moiety selected from the group consisting of carbonyl; carboxyalkyl; carboxamido, oxygen (as an ether); amino; thio; vinyl; and acetylenyl groups.

9. The compound of claim 5 wherein Y is a linear arrangement of 1-5 atoms which comprises a moiety selected from the group consisting of carbonyl; carboxyalkyl; carboxamido, oxygen (as an ether); amino; thio; vinyl; and acetylenyl groups.

10. The compound of claim 1 wherein Y is an alkylene of 1-5C substituted with sustituents selected from the group consisting of alkyl, hydroxyl, alkoxy, halogen, nitro, amino, cyano, caboxyalkyl, carboxamido, thio and alkylthio.

11. The compound of claim 5 wherein Y is an alkylene of 1-5C substituted with substituents selected from the group consisting of alkyl, hydroxyl, alkoxy, halogen, nitro, amino, cyano, caboxyalkyl, carboxamido, thio and alkylthio.

* * * * *